(12) United States Patent
Jaax et al.

(10) Patent No.: US 7,857,819 B2
(45) Date of Patent: Dec. 28, 2010

(54) IMPLANT TOOL FOR USE WITH A MICROSTIMULATOR

(75) Inventors: Kristen N. Jaax, Santa Clarita, CA (US); Rafael Carbunaru, Studio City, CA (US); James C. Makous, Santa Clarita, CA (US); Todd K. Whitehurst, Santa Clarita, CA (US); Meredith L. Anderson, Clifton Park, NY (US); Anne M. Pianca, Santa Monica, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 491 days.

(21) Appl. No.: 11/565,564

(22) Filed: Nov. 30, 2006

(65) Prior Publication Data

US 2008/0132961 A1    Jun. 5, 2008

(51) Int. Cl.
    *A61N 1/00* (2006.01)
(52) U.S. Cl. ..................................... 606/129
(58) Field of Classification Search .................. 607/116; 606/129
    See application file for complete search history.

(56) References Cited

U.S. PATENT DOCUMENTS

| | | | |
|---|---|---|---|
| 3,884,220 A | 5/1975 | Hartnett | |
| 4,136,702 A | 1/1979 | Trabucco | |
| 4,793,353 A | 12/1988 | Borkan | |
| 5,193,539 A | 3/1993 | Schulman et al. | |
| 5,193,540 A | 3/1993 | Schulman et al. | |
| 5,290,310 A | 3/1994 | Makower et al. | |
| 5,312,439 A | 5/1994 | Loeb | |
| 5,324,306 A | 6/1994 | Makower et al. | |

(Continued)

FOREIGN PATENT DOCUMENTS

WO    WO 98/37926    9/1998

(Continued)

OTHER PUBLICATIONS

Pathak et al. "Overactive bladder: drug therapy versus nerve stimulation" http://www.medscape.com/viewarticle/509777; Aug. 4, 2005; Medscape from WebMD.

(Continued)

*Primary Examiner*—George R Evanisko
(74) *Attorney, Agent, or Firm*—Frommer Lawrence & Haug LLP; Bruce E. Black

(57) ABSTRACT

A stimulation system is described that includes an implantable microstimulator. A tail may be coupled to a distal end of the implantable microstimulator. In one embodiment, the stimulation system includes an implantation tool that includes an insertion cannula, a handle, a bushing, and a detachable blunt dissector tip. The bushing is situated within the insertion cannula and may position the implantable microstimulator longitudinally within the insertion cannula when the implantable microstimulator is placed within the insertion cannula. The detachable blunt dissector tip may be attached to the tail of the implantable microstimulator. The stimulation system may further comprise an end cap that includes an upper portion and a base portion conformable over at least a portion of curved tissue. An open trough extends through the base upper portions and may be configured to guide the implantation tool through the tissue at various angles.

19 Claims, 6 Drawing Sheets

U.S. PATENT DOCUMENTS

| | | | |
|---|---|---|---|
| 5,405,367 A | 4/1995 | Schulman et al. | |
| 5,531,787 A | 7/1996 | Lesinski et al. | |
| 5,775,331 A | 7/1998 | Raymond et al. | |
| 5,817,061 A | 10/1998 | Goodwin et al. | |
| 6,051,017 A | 4/2000 | Loeb et al. | |
| 6,154,678 A | 11/2000 | Lauro | |
| 6,185,452 B1 | 2/2001 | Schulman et al. | |
| 6,214,032 B1 | 4/2001 | Loeb et al. | |
| 6,216,045 B1 | 4/2001 | Black et al. | |
| 6,235,001 B1 | 5/2001 | O'Holloran et al. | |
| 6,297,943 B1 | 10/2001 | Carson | |
| 6,306,125 B1 | 10/2001 | Parker et al. | |
| 6,482,179 B1 | 11/2002 | Chu et al. | |
| 6,582,441 B1 * | 6/2003 | He et al. | 606/129 |
| 6,609,032 B1 | 8/2003 | Woods et al. | |
| 6,671,554 B2 | 12/2003 | Gibson et al. | |
| 6,809,701 B2 | 10/2004 | Amundson et al. | |
| 6,845,267 B2 | 1/2005 | Harrison et al. | |
| 6,947,782 B2 | 9/2005 | Shulman et al. | |
| 7,203,548 B2 | 4/2007 | Whitehurst et al. | |
| 7,239,921 B2 | 7/2007 | Canfield et al. | |
| 7,292,890 B2 | 11/2007 | Whitehurst et al. | |
| 2003/0004546 A1 | 1/2003 | Casey | |
| 2003/0083728 A1 | 5/2003 | Greatbatch et al. | |
| 2004/0010296 A1 | 1/2004 | Swanson et al. | |
| 2004/0015204 A1 | 1/2004 | Whitehurst et al. | |
| 2004/0015205 A1 | 1/2004 | Whitehurst et al. | |
| 2004/0059392 A1 | 3/2004 | Parromon et al. | |
| 2005/0004619 A1 | 1/2005 | Wahlstrand et al. | |
| 2005/0240229 A1 | 10/2005 | Whitehurst et al. | |
| 2005/0251237 A1 * | 11/2005 | Kuzma et al. | 607/116 |
| 2005/0267555 A1 * | 12/2005 | Marnfeldt et al. | 607/116 |
| 2006/0161204 A1 | 7/2006 | Colvin et al. | |
| 2006/0167521 A1 | 7/2006 | He et al. | |
| 2006/0184204 A1 | 8/2006 | He et al. | |
| 2006/0195143 A1 | 8/2006 | McClure et al. | |
| 2006/0212087 A1 | 9/2006 | Haller et al. | |
| 2006/0229688 A1 | 10/2006 | McClure et al. | |
| 2006/0271109 A1 | 11/2006 | Kuzma et al. | |
| 2007/0021800 A1 | 1/2007 | Whitehurst et al. | |
| 2007/0049988 A1 | 3/2007 | Carbunaru et al. | |
| 2007/0066997 A1 | 3/2007 | He et al. | |
| 2007/0112403 A1 | 5/2007 | Moffitt et al. | |
| 2007/0112404 A1 | 5/2007 | Mann et al. | |
| 2007/0219595 A1 | 9/2007 | He et al. | |

FOREIGN PATENT DOCUMENTS

| | | |
|---|---|---|
| WO | WO 98/43700 | 10/1998 |
| WO | WO 98/43701 | 10/1998 |
| WO | WO 2007/059343 | 5/2007 |

OTHER PUBLICATIONS

Rice, Mike "Implantable Neurostimulation Device Market Poised for Explosive Growth" posted Jan. 7, 2006 Future Fab Intl. vol. 20 http://www.future-fab.com/documents.asp?d_ID=3725.

* cited by examiner

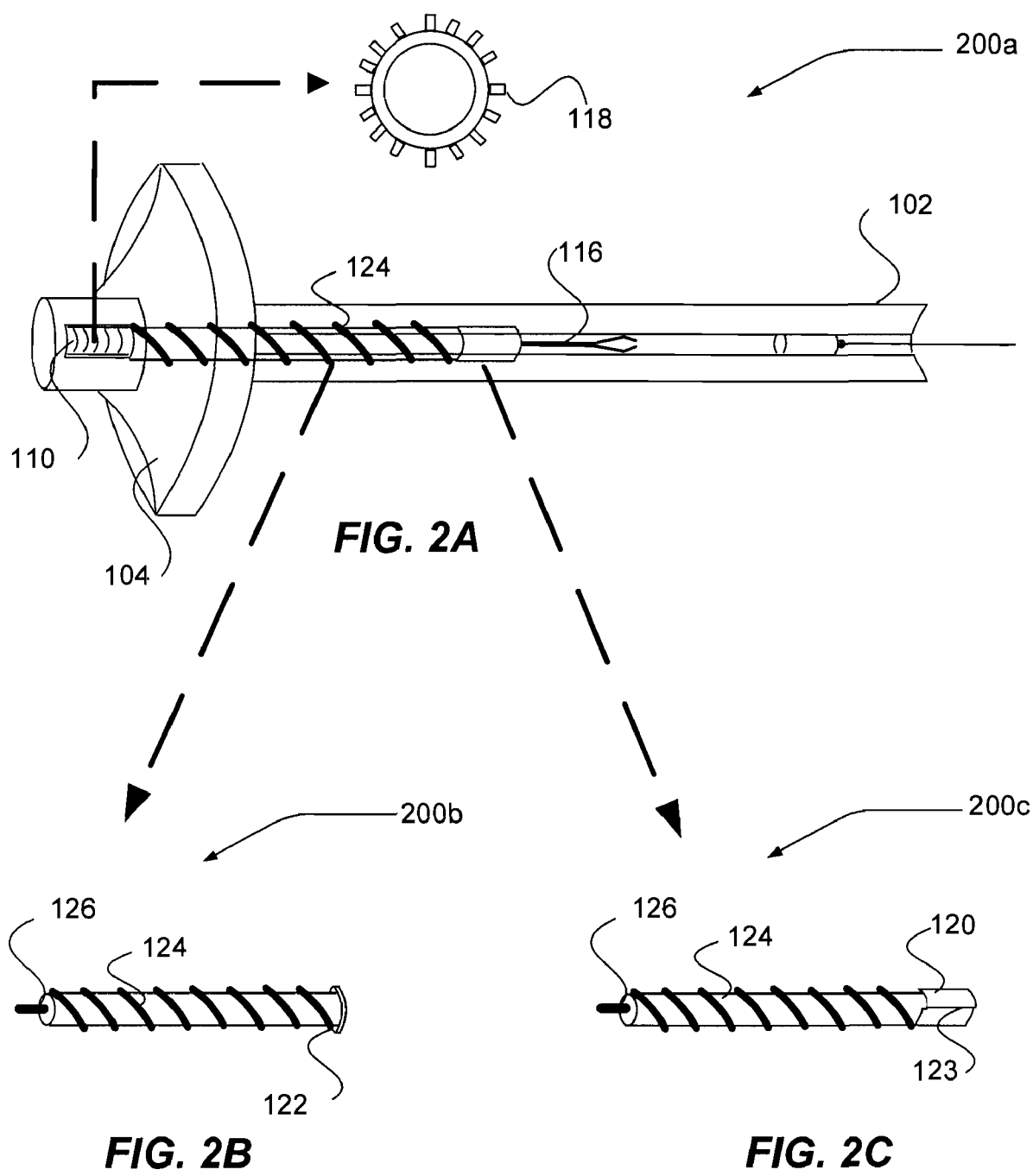

IMPLANT TOOL FOR USE WITH A MICROSTIMULATOR

FIELD OF THE INVENTION

The invention relates generally to implantable stimulation systems for neurostimulation, and more particularly, but not exclusively, to tools and methods for the insertion and/or implantation of electrode contacts, and electrodes of implantable microstimulator systems.

BACKGROUND OF THE INVENTION

Neurostimulation is the application of electrical stimulation to neurological pathways, such as nerve bundles, neurovascular bundles, and so forth. Electrical stimulation has a history in medicine for treating various ailments. For example, neurostimulation has been used for the treatment of chronic radiculopathy (sciatica), failed back syndrome, neuropathy, reflex sympathetic dystrophy (complex regional pain syndrome), and various vascular insufficiencies.

In addition, electrical stimulation has been used as a treatment for patients with urge incontinence caused by overactive bladders who do not respond to behavioral treatments or medications. In this procedure, an electrode lead with electrical contacts may be placed near the sacral nerve and passed under the tissue to a stimulator. Electrical pulses may then be sent to the sacral nerve, the nerve near the tailbone that influences bladder control muscles. Stimulation of this nerve may relieve the symptoms related to urge incontinence. Electrical stimulation has also been used to treat chronic migraine headaches.

Although the clinical efficacy of neurostimulation using implantable electrode contacts is well known, implantation is a surgical procedure that requires surgical training, and use of the proper implantation tools. However, many of today's tools used for inserting implantable electrode contacts may hinder the ease and success of many implants and/or explants. As a result, a patient may not receive proper neurostimulation because the electrode contact may have inadvertently moved from its intended position during implantation. Improper positioning of the electrode contact implant may account for longer charging time that some patients experience.

BRIEF SUMMARY OF THE INVENTION

One embodiment is a stimulation system for a nerve. The stimulation system includes an implantable microstimulator. The implantable microstimulator includes an electrode contact for stimulating tissue, and has a tail. The tail is coupled at a distal end of the implantable microstimulator. The tail is useable to constrain movement of the implantable microstimulator when the implantable microstimulator is positioned within tissue.

In another embodiment, the stimulation system includes an implantation tool. The implantation tool includes an insertion cannula, and a handle at a proximal end of the insertion cannula. The implantation tool further includes a bushing and a detachable blunt dissector tip. The bushing is situated within the insertion cannula and is arranged to position the implantable microstimulator longitudinally within the insertion cannula when the implantable microstimulator is placed within a lumen of the insertion cannula. The detachable blunt dissector tip is located at the distal end of the cannula and is attached to the tail of the implantable microstimulator.

In one embodiment, the stimulation system comprises an end cap. The end cap includes a base portion and an upper portion that is affixed to the base portion. The base portion may be conformable over at least a portion of curved tissue. The end cap further includes an open trough extending through the base portion and the upper portion that may be configured to guide the implantation tool through the tissue at various angles.

In another embodiment of the end cap, the end cap includes an attached cleat. The cleat may be configured to grip the tail upon removal of the detachable blunt dissector tip and to constrain movement of the electrode contact while the implantation tool is removed from the tissue.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 2A illustrates a cross-sectional view of one embodiment of a bushing-based advancing system using a threaded system within the implantation tool;

FIG. 2B illustrates one embodiment of the bushing-based advancing system of FIG. 2A with a bushing configured as a push plate;

FIG. 2C illustrates one embodiment of the bushing-based advancing system of FIG. 2A having an extended bushing;

DETAILED DESCRIPTION OF THE INVENTION

The present invention now will be described more fully hereinafter with reference to the accompanying drawings, which form a part hereof, and which show, by way of illustration, specific exemplary embodiments by which the invention may be practiced. This invention may, however, be embodied in many different forms and should not be construed as limited to the embodiments set forth herein. Among other things, the invention may be embodied as methods or devices. The following detailed description is, therefore, not to be taken in a limiting sense.

Throughout the specification and claims, the following terms take the meanings explicitly associated herein, unless the context clearly dictates otherwise. The phrase "in one embodiment" as used herein does not necessarily refer to the same embodiment, though it may. As used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

Briefly stated, the invention is directed towards a stimulation system for implanting of electrode contacts, as well as devices that include the electrode contacts, for nerve stimulation and treatment of other disorders. An implantation tool is described that functions to find a target location, insert, deploy, and extract an implantable microstimulator.

Figure 1A:
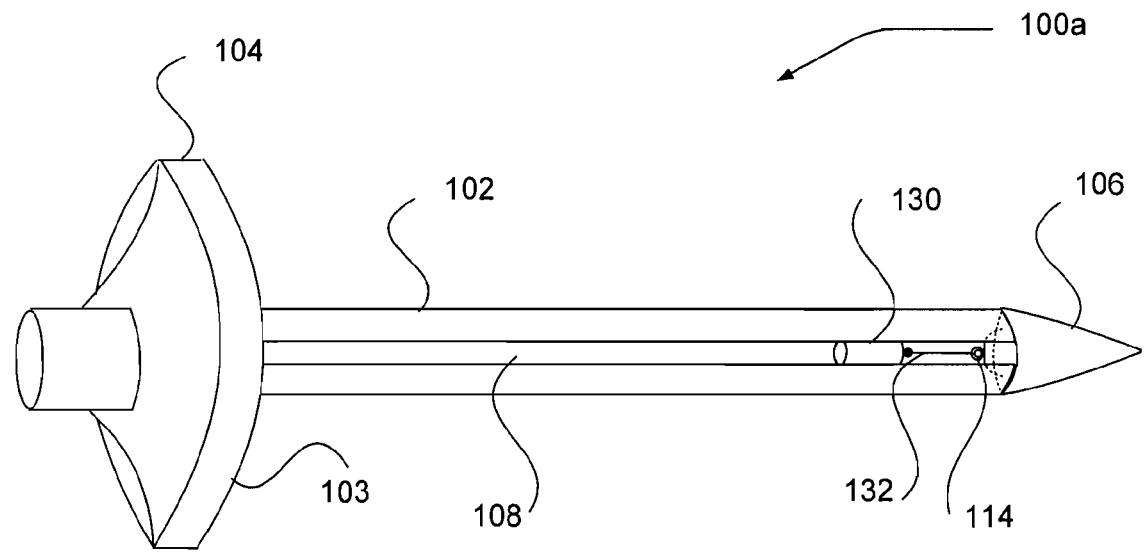
FIG. 1A shows a cross-sectional view of one embodiment of an implantation tool and implantable stimulator.

FIG. 1A shows a cross-sectional view of one embodiment of a stimulation system for use in implanting an implantable microstimulator. As shown in the figure, stimulation system 100a includes an implantation tool and an implantable microstimulator 130. In one embodiment, the implantation tool includes, in part, a handle 104, an insertion cannula 102, and a detachable blunt dissector tip 106. Also shown is an implantable microstimulator 130 that is coupled at its distal end to tail 132.

One embodiment of implantable microstimulator 130 is described in more detail below in conjunction with FIG. 6. Briefly, however, implantable microstimulator 130 represents any of a variety of implantable microstimulation devices designed for tissue stimulation. One embodiment of an implantable microstimulator is a BION® microstimulator of the type made by Advanced Bionics Corporation, California. Another embodiment of an implantable microstimulator is described in U.S. Pat. No. 5,312,439, which is incorporated herein by reference, and is entitled "Implantable Device Having an Electrolytic Storage Electrode." Other implantable microstimulators that may represent implantable microstimulator 130 include but are not limited to those described within U.S. Pat. No. 5,193,539, entitled "Implantable Microstimulator," and U.S. Pat. No. 5,193,540, entitled "Structure and Method of Manufacture of an Implantable Microstimulator," each of which are incorporated herein by reference. Further examples of suitable microstimulators are also described in U.S. Pat. Nos. 6,051,017; and 6,609,032; U.S. Patent Application Publication No. 2004/059392; U.S. patent application Ser. Nos. 11/040,209 and 11/056,762; and PCT Patent Applications Publication Nos. 98/37926; 98/43700; and 98/43701, all of which are incorporated herein by reference.

Implantable microstimulator 130 includes tail 132. In one embodiment, one end of tail 132 may be attached at a distal end of implantable microstimulator 130, while another end of tail 132 may be attached to a proximal end of blunt dissector tip 106. In one embodiment, tail 132 is arranged to be threaded through eyelet 114 at the proximal end of blunt dissector tip 106 to form a loop, with both ends of looped tail 132 being attached to the distal end of implantable microstimulator 130. The invention is not limited to employing an eyelet, however, and any of a variety of other mechanisms may be employed to couple tail 132 to the proximal end of blunt dissector tip 106.

In one embodiment, tail 132 may be of a length sufficient to enable removal of blunt dissector tip 106 upon insertion of the implantation tool through tissue, without perturbation of a position of implantable microstimulator 130 within the tissue. In one embodiment, such length may result in at least a portion of tail 132 being coiled or otherwise arranged between implantable microstimulator 130 and blunt dissector tip 106, within a lumen of cannula 102.

Tail 132 may comprise any material useable for suturing tissue, including but not limited to string, silk, cat gut, polyglactin (coated vicryl), polydioxanone, nylon (e.g., ethilon), polypropylene (prolene), or the like. Ideally, tail 132 comprises a biologically inert material. In one embodiment, tail 132 comprises suturing material arranged with a plurality of loops chained together to form an extended string of loops. Each loop may be configured to enable insertion of a needle through the loop. However, it is noted that tail 132 need not be arranged as a loop of material, and may also be a single portion of material coupled between blunt dissector tip 106 and implantable microstimulator 130.

In one embodiment, tail 132 may also be a lead wire that can be easily connected to a suitable external stimulation unit in order to allow for electrical conduction to implantable microstimulator 130. In one embodiment, tail 132 may be an insulated multi-filament conductor.

As illustrated in the figure, the implantation tool includes, in part, handle 104, which is situated at a proximal end of insertion cannula 102. Handle 104 may be configured to enable grasping and positioning of insertion cannula 102. The handle 104 may be constructed of a variety of materials including a silicone material, Teflon, metal coated with rubber, or the like. In one embodiment, handle 104 may comprise a material that is conformable to at least a portion of a curved tissue.

In one embodiment, handle 104 may comprise an approximately ring shaped structure that surrounds an exterior of insertion cannula 102 and is arranged to be movable along the exterior of insertion cannula 102. For example, in one embodiment, when insertion cannula 102 is inserted into the tissue, handle 104 may be positioned along the exterior of insertion cannula 102 to be flush with at least a portion of the tissue. Positioning of handle 104 may be achieved by sliding the handle 104 along the exterior of the insertion cannula 102, or by screwing the handle 104, or the like.

In one embodiment, handle 104 may include an adhesive material 103 on a relatively flat side 103a of the handle 104 that may be positioned to be in contact with tissue during insertion of insertion cannula 102 into the tissue. The adhesive material 103 may enable handle 104 to adhere to the tissue and stabilize the insertion cannula 102 during use.

Insertion cannula 102 is a tubular arrangement that has a lumen diameter sufficient to allow for the implantable microstimulator 130 to move freely along its inner length. Insertion cannula 102 may comprise silicone material, plastic, metal, or the like, or any combination thereof. In one embodiment insertion cannula 102 may include a slot 108 extending longitudinally along one side. The width of the slot may be smaller than a diameter of implantable microstimulator 130.

Although not shown in this figure for simplicity, the implantation tool may include a bushing-based advancing system that is arranged to position the implantable microstimulator 130 longitudinally within insertion cannula 102. Various embodiments of bushing-based advancing systems are described in more detail below in conjunction with FIGS. 2A-C, and 3A-B.

At its distal end, the implantation tool includes a detachable blunt dissector tip 106. Blunt dissector tip 106 may be inserted at least partially into the insertion cannula 102 of the implantation tool. As described above, the blunt dissector tip 106 may be attached to tail 132, such that removal of the blunt dissector tip 106 allows access to the tail 132, for example, to aid in suturing of the tail 132 to tissue or hold the microstimulator in place during removal of the insertion tool.

In one embodiment, blunt dissector tip 106 is shaped in an approximate cone shape with its proximal end being approximately circular in shape to fit within insertion cannula 102. The distal end of blunt dissector tip 106 may be narrower than its proximal end and may be slightly blunted to avoid or reduce damaging of tissue during insertion. In one embodiment, the distal end may be sharpened to enable dissection of tissue during insertion. In one embodiment, the distal end may be sharp like an arrow or needle.

Figure 1B:
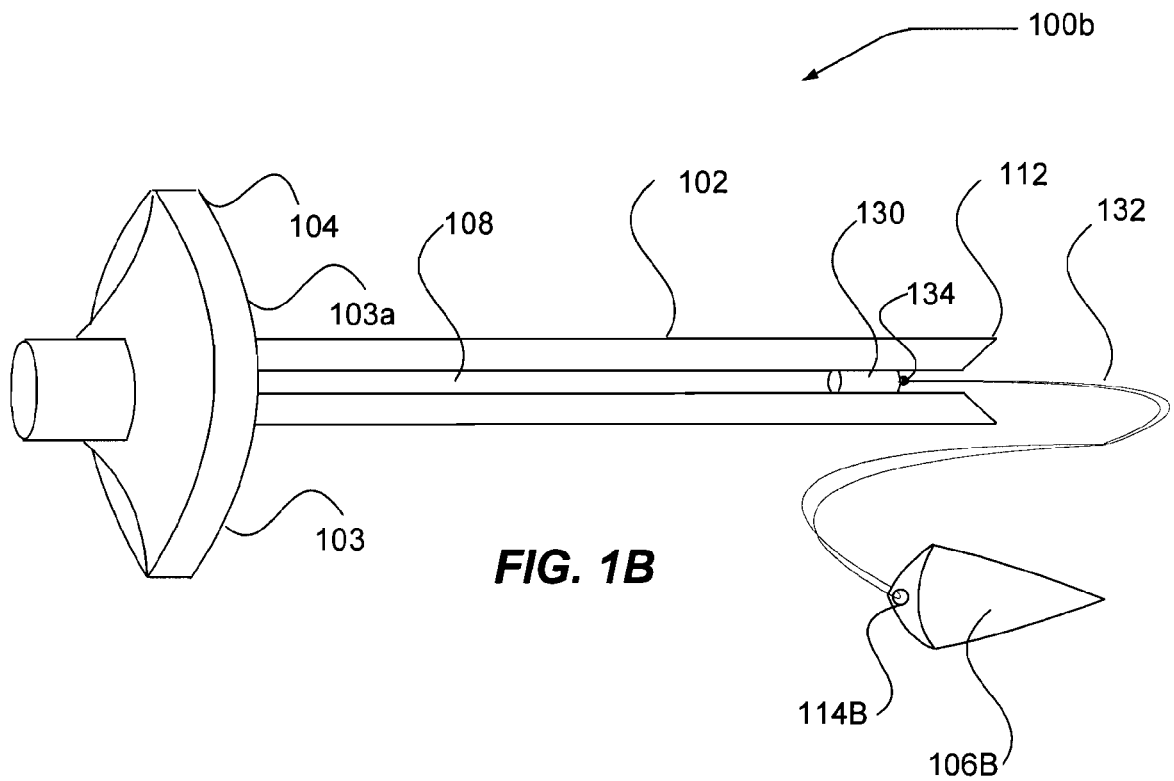
FIG. 1B illustrates in more detail the implantation tool of FIG. 1A with a blunt dissector tip removed.

FIG. 1B illustrates in more detail the implantation tool of FIG. 1A with its blunt dissector tip removed. As shown in the figure, stimulation system 100b includes the implantation tool and the implantable microstimulator 130. Also shown in the figure is a looped tail 132 embodiment, where both ends of the tail 132 are attached to the distal end of the implantable microstimulator 130. In this embodiment, tail 132 is shown looped through an opening 114B located within blunt dissector tip 106B and its proximal end. Tail 132 may be coupled to the blunt dissector tip through a variety of different mechanisms. For example, tail 132 may also be coupled to the blunt dissector tip through a clip mechanism, an adhesive material, or the like.

FIG. 2A illustrates a cross-sectional view of one embodiment of a bushing-based advancing system within a lumen of an implantation tool such as described above. System 200a illustrates one of several possible embodiments for a bushing-based advancing system useable to position the implantable microstimulator 130 longitudinally within the insertion cannula 102.

As shown in the figure, the bushing-based advancing mechanism may be located within the lumen of insertion cannula 102. System 200a also illustrates a turn mechanism 110. In one embodiment, turn mechanism 110 employs worm gear 118 within the lumen of insertion cannula 102 and situated around a proximal end of threaded system 124. The worm gear 118 may be exposed and accessible through an upper portion of insertion cannula 102, and/or handle 104. In addition, worm gear 118 may be constrained in its overall longitudinal movement. By rotating worm gear 118, the threaded system 124 may be made to move along the lumen of insertion cannula 102, and thereby advance or retreat a bushing within the lumen of insertion cannula 102 that is situated at a distal end of the threaded system 124. As the bushing advances along the lumen of insertion cannula 102, it may in turn move the implantable microstimulator 130 within a length of the insertion cannula 102.

Also shown in FIG. 2A is an optional grasping mechanism 116 at a distal end of threaded system 124. In one embodiment, optional grasping mechanism 116 may be coupled to the bushing situated at the distal end of threaded system 124. In another embodiment, the bushing may be removed and optional grasping mechanism 116 may be coupled directly to the distal end of threaded system 124. Optional grasping mechanism 116 may comprise a hook, claws, or the like, that are configured to grasp the implantable microstimulator 130 during extraction from tissue, for example. A button, trigger, or similar mechanism may be located on handle 104, or insertion cannula 102 to enable optional grasping mechanism 116 to be maneuvered to grasp and/or release implantable microstimulator 130.

In one embodiment, optional grasping mechanism 116 may be completely removed from the insertion tool, such as illustrated in FIGS. 3A, and 5A-5D.

FIG. 2B illustrates a cross-sectional view of one embodiment of the bushing-based advancing system 200b using a threaded system 124 with a bushing configured as a push plate 122. FIG. 2C illustrates one embodiment of a bushing-based advancing system 200c using a threaded system 124 having an extended bushing 120. As shown in FIG. 2C, one embodiment of a bushing includes a keying 123 configuration that is arranged to align the bushing within the lumen of insertion cannula 102. For example, in one embodiment, the keying 123 of the bushing may be positioned within slot 108.

Also shown in FIGS. 2B-C, bushing-based advancing systems 200b and 200c may include plunger 126. Plunger 126 may be a tube, pipe, or the like, situated within a lumen of threaded system 124 and extending beyond threaded system 124. Plunger 126 may be arranged such that it may slide within the lumen of threaded system 124 to push the implantable microstimulator 130, and thereby extend a reach of threaded system 124.

Figure 3A:
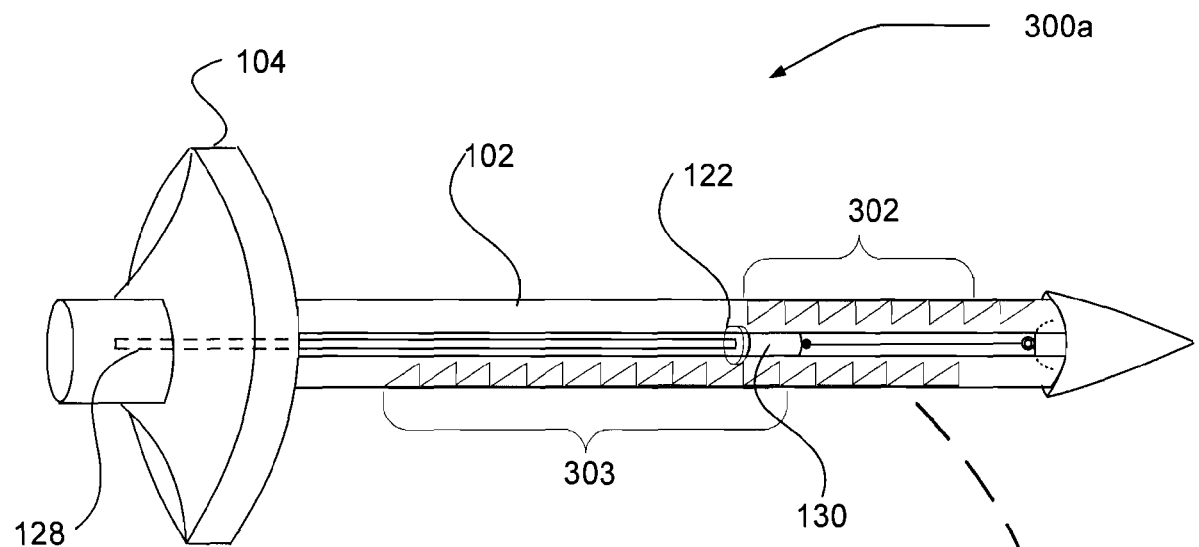
FIG. 3A illustrates one embodiment of an implantation tool that includes a plunger ratchet advancing system as another embodiment of a bushing-based advancing system.

FIG. 3A illustrates one embodiment of an implantation tool that includes a plunger ratchet advancing system as a bushing-based advancing system. Implementation system 300a shows plunger 128 within the lumen of the insertion cannula 102 and having coupled at its distal end bushing plate 122. Also shown are ratcheting teeth 302-303 that are positioned within and along at least a first portion and a second portion of the lumen of insertion cannula 102. In one embodiment, ratcheting teeth 302-303 extend substantially an entire length of insertion cannula 102. In another embodiment, ratcheting teeth 302-303 extend less than an entire length of insertion cannula 102. In one embodiment, bushing plate 122 may be configured to grip or otherwise be temporarily attached to implantable microstimulator 130. In this manner, retraction of plunger 122 within insertion cannula 102 may also retract implantable microstimulator 130. In one embodiment, a release button, trigger, or the like, (not shown) may be located on the implantation tool to release the grip on the implantable microstimulator 130.

Ratcheting teeth 302-303 may be constructed as a unitary part of insertion cannula 102 or constructed separately, and affixed within the inner wall of insertion cannula 102 using any of a variety of mechanisms, including chemical bonding, heat bonding, or the like.

In one embodiment, by rotating the bushing plate 122 the plunger 128 may be made to advance or to retreat within the insertion cannula 102. In one embodiment, at least a portion of bushing plate 122 may be flattened or otherwise shaped to allow motion in one direction within the insertion cannula 102, while a non-flattened portion of the bushing plate 122 prevents motion in an opposing direction within insertion cannula 102. When the bushing plate is rotated within the insertion cannula 102 the orientation of the flattened and non-flattened portions with respect to the ratcheting teeth 302-303 may be changed. By changing the orientation, the flattened portion may allow a movement in one direction, while a non-flattened portion of the bushing plate 122 prevents movement in the other direction along the insertion cannula 102. In one embodiment, the flattened portion may prevent movement by its contact with one set of ratcheting teeth 302 or 303. Thus, by varying the relationship of the flattened and non-flattened portions of the bushing plate 122 with respect to the ratcheting teeth 302-303, a position of plunger 128 may be changed along the lumen of insertion cannula 102, and the implantable microstimulator 130 may be positioned within the length of insertion cannula 102.

Figure 3B:
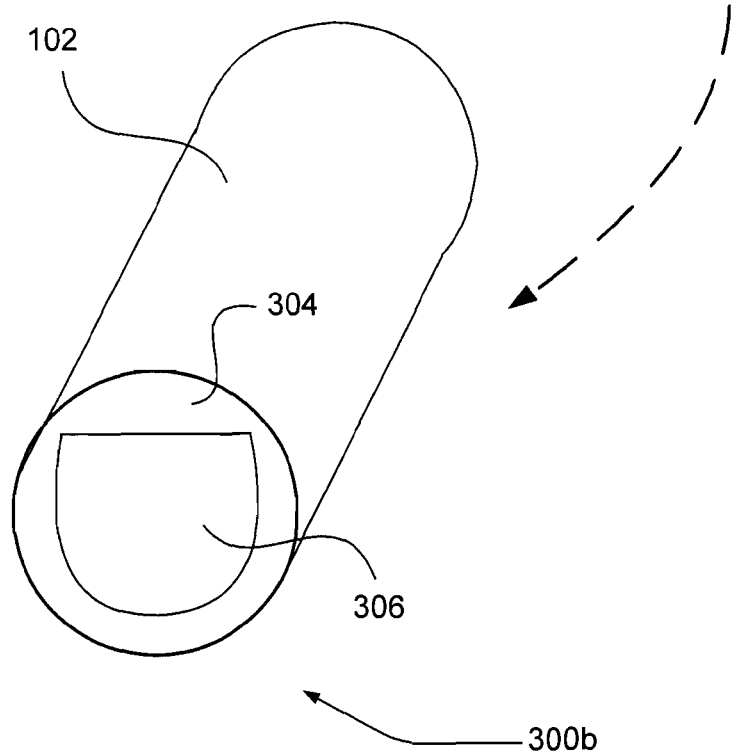
FIG. 3B illustrates another view of the plunger ratchet advancing system of FIG. 3A.

FIG. 3B illustrates another cross-sectional view of the plunger ratchet bushing-based advancing system of FIG. 3A. As shown in the figure, system 300b illustrates ratcheting teeth 304 within lumen 306 of insertion cannula.

Figure 4A:
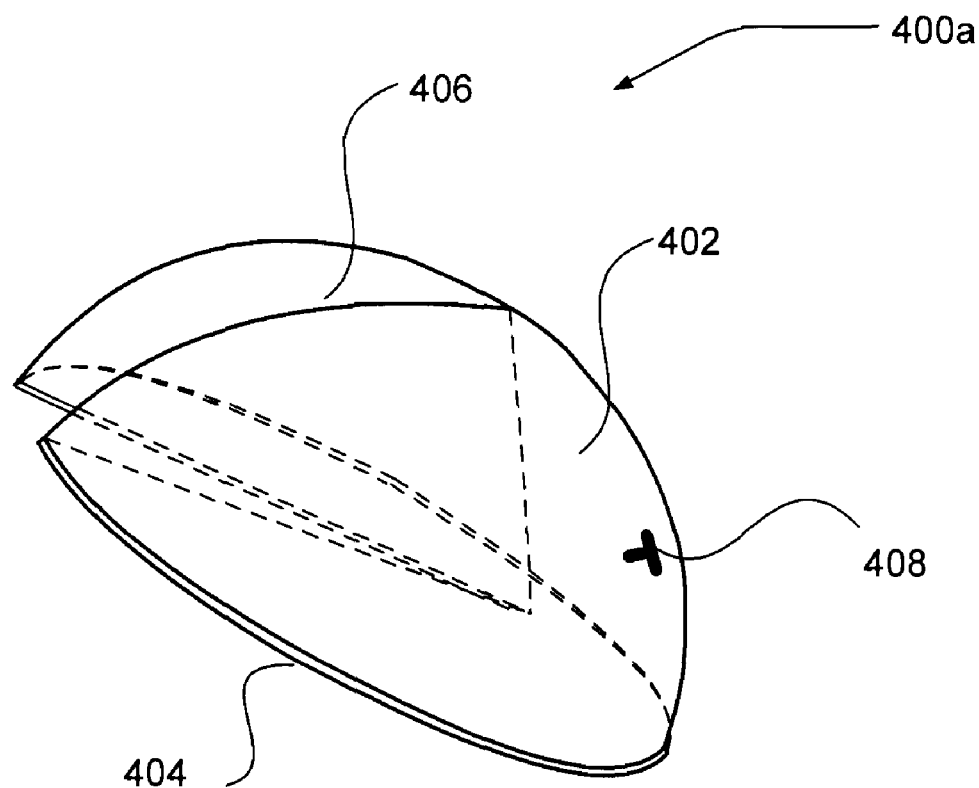
FIG. 4A illustrates one embodiment of an end cap for use with the stimulation system.

FIG. 4A illustrates one embodiment of an end cap for use with the stimulation system. End cap 400a may include many or fewer components than those shown. Although the components shown are sufficient to disclose an illustrative embodiment for practicing the invention, not all of these components may be required to practice the invention and variations in the arrangement and type of the components may be made without departing from the spirit or scope of the invention.

As shown in the figure, end cap 400a includes an upper portion 402, base portion 404, and an open trough 406. Open trough 406 may be configured to extend through the base portion 404 and upper portion 402 to guide an implantation tool through the end-cap 400a at various angles to the base portion 404.

In one embodiment, end cap 400a may be made of a material that allows the end cap 400a to conform over at least a portion of curved tissue. Thus, in one embodiment, end cap 400a may be made of formable Teflon, rubber, silicone, or the like. In one embodiment, base portion 404 may include a substance that enables the end cap 400a to adhere to the tissue to restrict movement during usage, but also allows removal.

Although end cap 400a is illustrated having approximately a dome shape, the invention is not so constrained, and end cap 400a may also be approximately oval in shape, cone shaped, parallelepiped, approximately box shaped, or any of a variety of other shapes that may include open trough 406. In one embodiment, end cap 400a may be hollow. In another embodiment, end cap 400a may be composed of an approximately solid structure. Also, although open trough 406 is illustrated approximately as a pie shaped opening, having angled inner sides the invention may have a tubular open trough shape with angled inner sides.

Also shown, end cap 400a includes an optional cleat 408 projecting from upper portion 402. Cleat 408 may be configured to allow tail 132 of implantable microstimulator 130 to be wrapped around. Although illustrated as a cleat, cleat 408 is not so limited, and virtually any mechanism that may be configured on end cap 400a to receive and hold tail 132 may be employed. Thus, for example, clear 408 may also represent a hook, a binder clip, a screw, an eyelet, or the like.

Figure 4B:
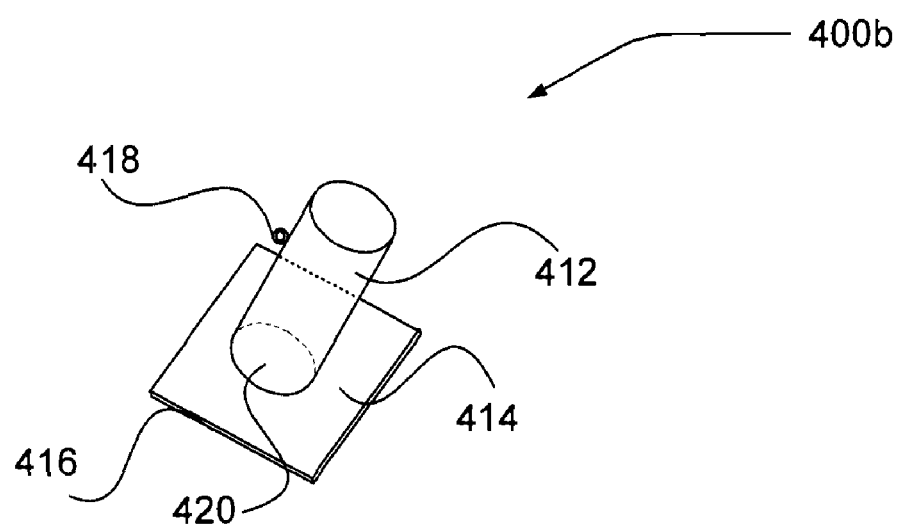
FIG. 4B illustrates another embodiment of another end cap for use with the stimulation system.

FIG. 4B illustrates another embodiment of an end cap for use with the stimulation system. End cap 400b of FIG. 4B includes base portion 414, upper portion 412 and an adhesive portion 416. Upper portion 412 is attached at its proximal end to base portion 414, with its proximal end extending outward approximately perpendicular to the base portion 414. Also shown is open trough 420 extending through the base portion 414 and the upper portion 412.

As shown, base portion 414 is approximately rectangular in shape, while upper portion 412 is approximately tubular in shape. However, as noted above, the invention is not limited to these shapes. In one embodiment, upper portion 412 may have a narrower opening at its proximal end than at its distal end.

Also illustrated, end cap 400b includes cleat 418 illustrated as an eyelet and affixed to an outer side of the upper portion 412. However, cleat 418 may also be affixed to one side of base portion 414 without departing from the scope of the invention.

Figure 5A:
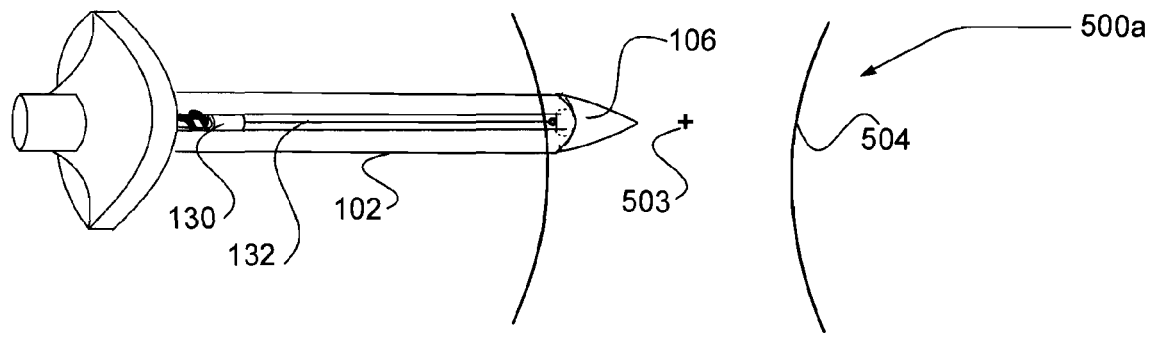
FIG. 5A-5D illustrate one embodiment of a method for using the stimulation system to insert an implantable microstimulator within tissue.

FIGS. 5A-5D illustrate one embodiment of a method (that includes operations 500a-500d) for using the implantation tool to insert an implantable microstimulator within tissue. In FIG. 5A, the implantable microstimulator 130 is positioned within the lumen of insertion cannula 102 of the implantation tool. The blunt dissector tip 106 of the implantation tool may then be inserted into tissue 504. The implantation tool is used to place the implantable microstimulator 130 at the target tissue location 503 within the tissue 504. Although not shown, in one embodiment, an end cap such as described above in conjunction with FIG. 4B may be placed over an ingress site on the tissue 504. The implantation tool may then be inserted through the end cap's open trough and into the underlying tissue 504. In another embodiment, as the implantation tool enters the tissue 504, the handle of the implantation tool may be repositioned along the insertion cannula 102 so as to contact and adhere to the tissue 504, and operate to stabilize lateral motion of the implantation tool.

In one embodiment, an agent may be injected into the target tissue location 503 to stabilize potential movement of the tissue 504 surrounding the target tissue location 503. The agent that is injected may include for example, collagen, hyaluronic acid, saline, or the like.

Figure 5B:
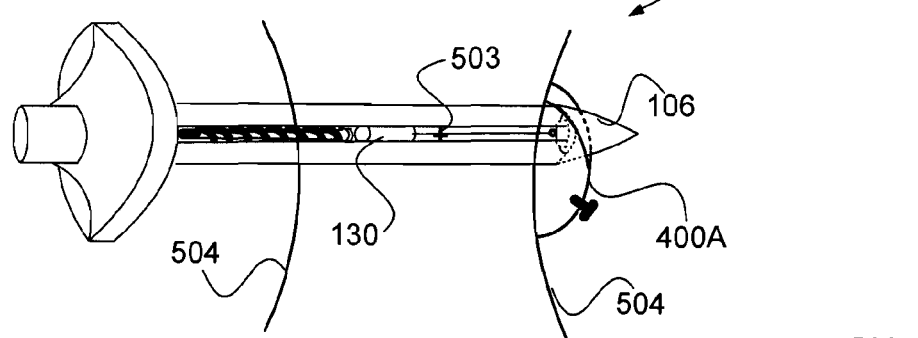

As shown in FIG. 5B, the insertion cannula 102 may be navigated through the tissue 504, and in one embodiment, the blunt dissector tip 106 may be used to penetrate or cut the tissue 504 and exit the tissue 504. Using an embodiment of the bushing-based advancing system the implantable microstimulator 130 may also be moved along within the lumen of the insertion cannula 102 to the target tissue location 503. As shown in FIG. 5B, an end cap 400a may be placed at an expected egress point on the tissue 504. The open trough extending through the end cap may be used to guide the insertion cannula 102 through the tissue 504, and to further restrict insertion cannula 102's additional movements while employing the bushing-based advancing system.

Figure 5C:
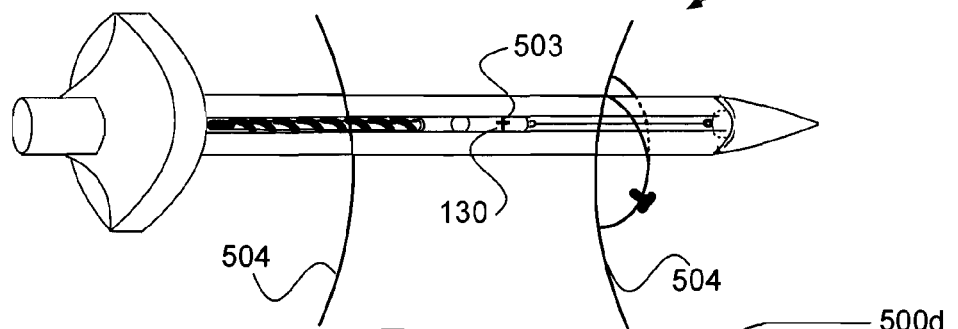
Figure 5D:
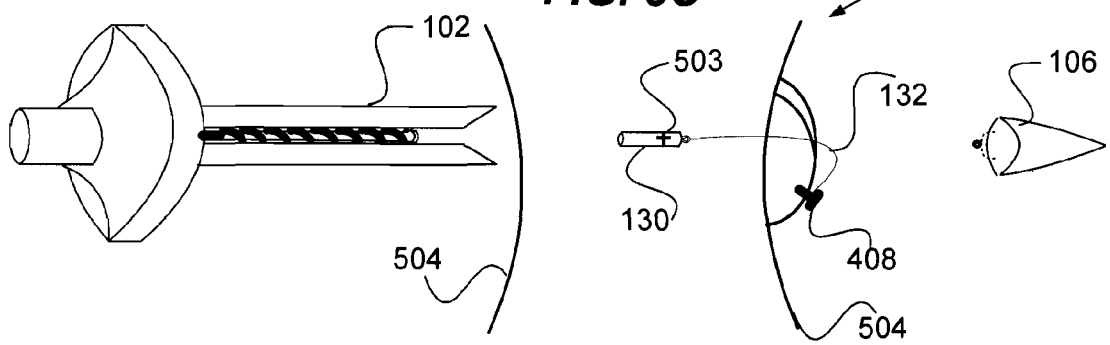

Once the implantable microstimulator 130 is at the target tissue location 503, as shown in FIG. 5C, the blunt dissector tip 106 may be detached from the implantation tool. The tail 132 may then be accessed. In one embodiment, as shown in FIG. 5D, the tail 132 may be detached from the blunt dissector tip 106 and fastened to cleat 408 on the end cap 400a. By fastening the tail 132 to the cleat 408, the tail 132 may constrain movement of the implantable microstimulator 130 while the implantation tool is removed from the tissue 504. In one embodiment, the tail 132 may be sutured to the tissue 504, and the end cap 400a may be removed. In one embodiment, where the tail 132 is a wire useable to conduct electrical signals to the implantable microstimulator 130, the tail 132 may also be connected to an external stimulation component, as is described below in conjunction with FIG. 6.

Figure 6:
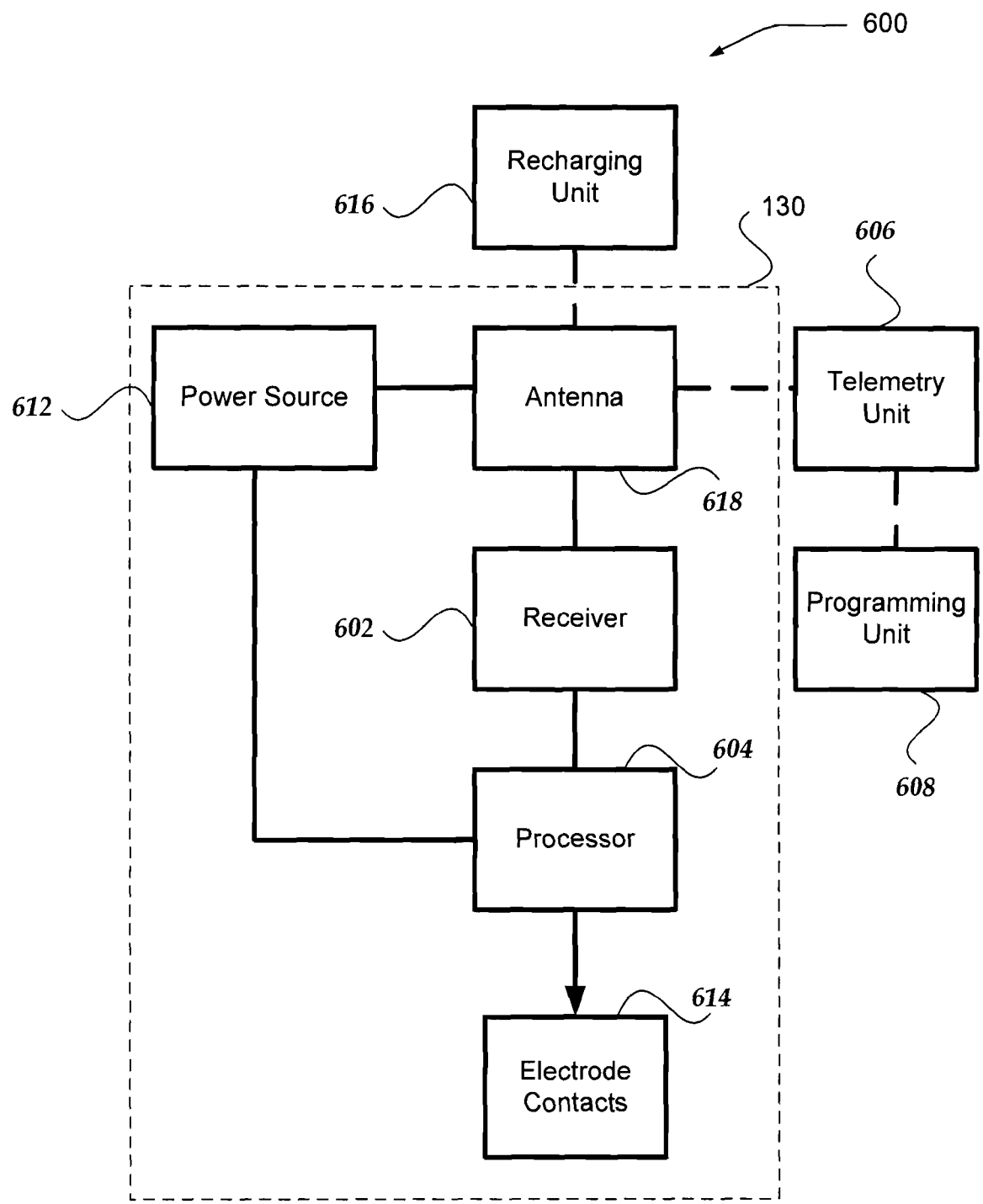
FIG. 6 illustrates a schematic cross-sectional view of one embodiment of a microstimulation assembly.

FIG. 6 illustrates a schematic cross-sectional view of one embodiment of a microstimulation assembly 600. Microstimulation assembly 600 may include many more or less components than those shown. Although the components shown are sufficient to disclose an illustrative embodiment for practicing the invention, not all of these components may be required to practice the invention and variations in the arrangement and type of the components may be made without departing from the spirit or scope of the invention.

Microstimulation assembly 600 includes implantable microstimulator 130, recharging unit 616, telemetry 606, and programming unit 608. In one embodiment, implantable microstimulator 130 is referred to as a stimulator unit, or as a portion of a stimulator unit (e.g., a portion of an implantable pulse generator).

Some or all of the components of microstimulation assembly 600 can be positioned on one or more circuit boards or similar carriers within housing of a stimulator unit if desired. Thus, in one embodiment, implantable microstimulator 130 may further include within it, one or more of power source 612, telemetry unit 606, programming unit 608, and/or recharging unit 616, without departing from the scope or spirit of the invention.

Any power source 612 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bio-energy power sources, fuel cells, bioelectric cells, osmotic pressure pumps, and the like including the power sources described in U.S. Patent Application Publication No. 2004/0059392, which is incorporated herein by reference.

As another alternative, power can be supplied by an external power source through inductive coupling via an optional antenna 618 or a secondary antenna (not shown). The external power source can be in a device that is mounted on the tissue of the user or in a unit that is provided near the stimulator user on a permanent or periodic basis.

If the power source 612 is a rechargeable battery, the battery may be recharged using the optional antenna 618, if desired. Power can be provided to the battery for recharging by inductively coupling the battery through the antenna to a recharging unit 616 external to the user.

In one embodiment, electrical current is emitted by the electrode contacts 614 to stimulate motor nerve fibers, muscle fibers, or other body tissues near the electrodes. The implantable microstimulator 130 provides the electronics used to operate the stimulator and generate the electrical pulses at the electrode contacts 614 to produce stimulation of the body tissues.

In the illustrated embodiment, a processor 604 is generally included in the implantable microstimulator 130 to control the timing and electrical characteristics of the stimulator. For example, the processor can, if desired, control one or more of the timing, frequency, strength, duration, and waveform of the pulses. In addition, the processor 604 can select which electrode contacts can be used to provide stimulation, if desired. In some embodiments, the processor may select which electrode contact(s) are cathodes and which electrode contact(s) are anodes. In some embodiments, the processor may be used to identify which electrode contacts provide the most useful stimulation of the desired tissue. This process may be performed using an external programming unit that is in communication with the processor 604.

Any processor can be used and can be as simple as an electronic device that produces pulses at a regular interval or the processor can be capable of receiving and interpreting instructions from an external programming unit 608 that allow modification of pulse characteristics. In the illustrated embodiment, the processor 604 is coupled to a receiver 602 which, in turn, is coupled to the optional antenna 618. This allows the processor to receive instructions from an external source to direct the pulse characteristics and the selection of electrode contacts, if desired.

In one embodiment, the antenna 618 is capable of receiving signals (e.g., RF signals) from an external telemetry unit 606 which may be programmed by a programming unit 608. The programming unit 608 can be external to, or part of, the telemetry unit 606. The telemetry unit 606 can be a device that is worn on the tissue of the user or can be carried by the user and can have a form similar to a pager or cellular phone, if desired. As another alternative, the telemetry unit may not be worn or carried by the user but may only be available at a home station or at a clinician's office. The programming unit 608 can be any unit that can provide information to the telemetry unit for transmission to the stimulator. The programming unit 608 can be part of the telemetry unit 606 or can provide signals or information to the telemetry unit via a wireless or wired connection. One example of a suitable programming unit is a computer operated by the user or clinician to send signals to the telemetry unit.

The signals sent to the processor 604 via the antenna 618 and receiver 602 can be used to modify or otherwise direct the operation of the stimulator. For example, the signals may be used to modify the pulses or pre-pulses of the stimulator such as modifying one or more of pulse duration, pulse frequency, pulse waveform, and pulse strength. The signals may also direct the stimulator to cease operation or to start operation or to start charging the battery. In other embodiments, the implantable microstimulator 130 does not include an antenna 618 or receiver 602 and the processor 604 operates as programmed.

Optionally, the implantable microstimulator 130 may include a transmitter (not shown) coupled to the processor and antenna for transmitting signals back to the telemetry unit 606 or another unit capable of receiving the signals. For example, the implantable microstimulator 130 may transmit signals indicating whether the implantable microstimulator 130 is operating properly or not or indicating when the battery needs to be charged. The processor may also be capable of transmitting information about the pulse characteristics so that a user or clinician can determine or verify the characteristics.

The optional antenna 618 can have any form. In one embodiment, the antenna 618 comprises a coiled wire that is wrapped at least partially around the implantable microstimulator 130 within or on the housing.

Any method of manufacture of the components of the system for stimulation can be used. Particular components such as, the electronic subassembly, power source, and antenna, can be placed inside a housing (or, alternatively, the housing can be formed, e.g., molded, around the components) to form an implantable pulse generator.

A stimulator can be implanted into a patient and electrical signals can be provided to the conductive electrode contact(s) 614 to stimulate a tissue. In one embodiment, a method of using an implantable stimulator includes implanting an implantable stimulator comprising a conductor. The conductor may comprise electrode contacts 614 that are disposed at a distal end of the conductor. Electrode contacts 614 may be arranged as described above. An electrical signal is provided to at least one electrode contacts 614 to stimulate a tissue. Moreover, implantable microstimulator 130 can be implanted into the body tissue using a variety of methods including surgical methods as described above in conjunction with FIGS. 5A-5D.

The electrode contacts 614 may be selectively stimulated. Electrical signals may be provided to the electrode contacts 614 of the stimulator simultaneously. Alternatively, electrical signals can be provided to the electrode contacts 614 of the stimulator independently of one another. Coordination of the electrical signals provided to the electrode contact (s) 614 is often facilitated by a processor 604.

The microstimulation assembly 600 may be used to provide various electrical signals to the electrode contacts 614 arranged within it or optionally, external to it, to stimulate the nerve, or other fiber, including, but not limited to pre-pulsing stimulations, or other waveform stimulations. In one embodiment, the electrical signals may be applied to provide a hybrid of depth stimulations. In another embodiment, the electrical signals may be applied on different timing channels to the electrode contacts.

The above specification, examples, and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A stimulation system, comprising:
   an insertion tool comprising
      an insertion cannula,
      a handle at a proximal end of the insertion cannula for grasping the insertion cannula,
      a bushing-based advancing mechanism situated within the insertion cannula and comprising a bushing arranged to push the implantable microstimulator longitudinally within the insertion cannula when the implantable microstimulator is placed within a lumen of the insertion cannula,
      a detachable blunt dissector tip at the distal end of the cannula, and
      a tail attached to the detachable blunt dissector tip, and
   an implantable microstimulator with the tail coupled at a distal end of the implantable microstimulator and useable to constrain movement of the implantable microstimulator within tissue, wherein the microstimulator comprises a housing, a power source disposed within the housing, and at least one electrode disposed on the housing.

2. The stimulation system of claim 1, wherein the insertion tool further comprises:
   a grasping mechanism attached to a distal end of the bushing-based advancing mechanism for use in grasping the implantable microstimulator.

3. The stimulation system of claim 1, wherein the handle is configured to be moveable along an exterior of the insertion cannula.

4. The stimulation system of claim 1, wherein the bushing-based advancing mechanism further comprises:
   a threaded system situated longitudinally within the lumen of the cannula, the bushing being attached to a distal end of the threaded system, and
   wherein the handle further comprises a thumbwheel for moving the threaded system and thereby positioning the bushing longitudinally along the cannula.

5. The stimulation system of claim 4, wherein the bushing-based advancing mechanism further comprises a plunger running longitudinally within a lumen of the threaded system and is configured to further position the bushing longitudinally along the cannula.

6. The stimulation system of claim 4, wherein the bushing is keyed.

7. The stimulation system of claim 1, wherein the bushing comprises a bushing plate and the bushing-based advancing mechanism further comprises:
   a plurality of ratcheting teeth situated longitudinally within the lumen of the insertion cannula; and
   a plunger that is coupled at a distal end to the bushing plate and is arranged to ratchet the bushing plate longitudinally within the lumen of the insertion cannula and across the plurality of ratcheting teeth.

8. The stimulation system of claim 1, further comprising:
   an end cap comprising:
      a base portion that is conformable over at least a portion of curved tissue;
      an upper portion affixed to the base portion;
      an open trough extending through the base portion and the upper portion and configured to guide an implantation tool through the tissue at various angles; and
      an optional cleat attached to one or more of the base portion or the upper portion of the end cap and configured to grip the tail upon removal of the detachable blunt dissector tip and to constrain movement of the implantable microstimulator while the implantation tool is removed from the tissue.

9. The stimulation system of claim 8, wherein the base portion of the end cap is further configured to adhere to the tissue.

10. The stimulation system of claim 8, wherein the curved upper portion of the end cap is shaped in an approximately hemispherical shape.

11. The stimulation system of claim 8, wherein the base portion of the end cap further comprises a silicone material.

12. The stimulation system of claim 1, wherein the tail is threaded through a proximal end of the detachable blunt dissector tip.

13. The stimulation system of claim 1, wherein the tail further comprises a conductor wire.

14. The stimulation system of claim 1, further comprising:
   a plate having a cylindrical hollow tube mounted through the plate, the plate being configured to be placed over an implant region of tissue and to minimize a lateral movement of an implantation tool when inserted longitudinally through the cylindrical hollow tube.

15. The stimulation system of claim 1, wherein the tail is a string.

16. The stimulation system of claim 15, wherein the string comprises silk, cat gut, polyglactin, polydioxanone, nylon, or polypropylene.

17. The stimulation system of claim 15, wherein the tail further comprises a conductor wire.

18. A method for implanting an implantable microstimulator into tissue, the method comprising:
   providing the stimulation system of claim 1;
   securing an end cap at an egress site on the tissue, the end cap having an open trough extending through the end cap and being configured to guide the insertion cannula of the insertion tool through the tissue at various angles;
   placing the implantable microstimulator within the insertion cannula;
   inserting the insertion cannula through the tissue at an ingress site and through the egress site such that the distal end of the insertion cannula is guided along the open trough of the end cap;
   positioning the implantable microstimulator at a desired target location within the tissue using the bushing-based advancing mechanism to advance the implantable microstimulator within the insertion cannula;
   attaching the tail to the end cap, in part, by removing the detachable blunt dissector tip upon egress from the tissue; and
   removing the insertion cannula from the tissue while the implantable microstimulator remains at the desired target location.

19. The method of claim 18, further comprising: injecting a stabilizing agent into the tissue to constrain mechanical movement of the tissue during implantation of the implantable microstimulator.

* * * * *